United States Patent [19]

Miller et al.

[11] Patent Number: 5,246,861
[45] Date of Patent: Sep. 21, 1993

[54] USE OF NONRADIOACTIVE COMPLEX METAL ANION AS TRACER IN SUBTERRANEAN RESERVOIRS

[75] Inventors: John F. Miller; Clyde O. Sheely; Jerry W. Wimberley, all of Ponca City; Rhea A. Howard, Stillwater, all of Okla.

[73] Assignee: Conoco Inc., Ponca City, Okla.

[21] Appl. No.: 893,625

[22] Filed: Jun. 5, 1992

[51] Int. Cl.$^5$ ............... G01N 33/20; G01N 33/24; E21B 47/00; E21B 49/00
[52] U.S. Cl. ........................... 436/27; 436/25; 436/56; 436/73; 436/84; 166/250; 166/268; 166/275
[58] Field of Search ............ 436/27, 29, 56, 85, 436/2, 25, 30-31, 155, 173-4, 176-7, 73, 84; 166/250, 268, 275, 300

[56] References Cited

U.S. PATENT DOCUMENTS

| | | |
|---|---|---|
| 3,003,856 | 10/1981 | Boyd . |
| 3,112,182 | 11/1963 | Brown ..................... 436/27 |
| 3,507,620 | 4/1970 | Gurney .................... 436/27 |
| 3,508,875 | 4/1970 | Sandiford ................. 436/25 |
| 4,352,674 | 10/1982 | Fery ........................ 436/27 |
| 4,782,899 | 11/1988 | Richardson .............. 166/252 |
| 5,082,569 | 1/1992 | Homeier et al. ......... 210/679 |

OTHER PUBLICATIONS

Hodge et al., "Determination of Platinum and Iridium in Marine Waters, Sediments, and Organisms", *Analytical Chemistry*, 1986, vol. 58, 616-620.

Heisler, "Interpretation of Radioactive tracer Results in a Steamdrive Project", 56th SPE CA. Reg. Annual Meeting Proc. N15092 vol. 2 15-28, 1986.

Lebecka et al., "The application of tripotassium-hexacyanide-60 . . . ", Rap.-Inst. Fiz. Tech. Jad. 196/I 35-49.

Lebecka et al., "Tracing of underground waters by means of K360Co(CN)", Freiberg, Forschungsh, C417 155-9.

Pablo, "Radiotrader adsorption study on Baguio soils", Phillipp Noel. J. 2(2) 211-14.

Drabaek, "Analysis and time stability of activable hydrospheric tracers", Journal Radioanal Chem. vol. 75, 97-106.

*Primary Examiner*—James C. Housel
*Assistant Examiner*—Robert Carpenter
*Attorney, Agent, or Firm*—Richard W. Collins

[57] ABSTRACT

Complex metal anions such as cobaltic hexacyanide are utilized as nonradioactive tracers in reservoir studies. Sensitive analytical procedures enable detection and measurement of very low tracer levels.

6 Claims, No Drawings

USE OF NONRADIOACTIVE COMPLEX METAL ANION AS TRACER IN SUBTERRANEAN RESERVOIRS

BACKGROUND OF THE INVENTION

Knowledge of reservoir behavior is important in planning and carrying out secondary and enhanced recovery processes in oil reservoirs. The use of chemical and radioactive tracers for reservoir evaluation has been thoroughly developed over the past few decades. In tracer studies, an identifiable tracer material is injected through one or more injection wells into the reservoir being studied. Water or other fluid is then injected to push the tracer to one or more recovery wells in the reservoir. The output of the recovery wells is monitored to determine tracer breakthrough and flow through the recovery well(s). Analysis of the breakthrough times and flows yields important information for use in carrying out the secondary or enhanced recovery process.

Most of the previously used tracers have been radioactive compounds. Output from recovery wells has been monitored for radioactivity to determine tracer breakthrough and flow.

In recent years, environmental and safety considerations have drastically impacted the use of radioactive tracers, and there has been a need for effective nonradioactive tracers for reservoir studies.

Nonradioactive tracers have been proposed, for example as described in U.S. Pat. No. 3,003,856 to Boyd, but have disadvantages in that the amount of tracer injected needs to be quite high in order to be detected during analysis of output from the recovery wells. Additionally, many chemical tracers are subject to reaction with materials in the reservoir, hindering their effectiveness.

There has been a need for chemical tracers that are safe, readily available, environmentally acceptable and detectible in very low amounts, so that small amounts can be injected and yet breakthrough and flow can be accurately measured. Such tracers are provided by the present invention.

SUMMARY OF THE INVENTION

In accordance with this invention, nonradioactive complex metal anions that can be detected in very low concentrations are used as tracers in reservoir studies.

DESCRIPTION OF THE PREFERRED EMBODIMENTS

The nonradioactive tracers useful in this invention are complex metal anions. Preferred tracers are the water soluble salts of cobaltic hexacyanide such as sodium, potassium or ammonium cobaltic hexacyanide. The cobalt in the tracer compound in this invention must be in the complex anion portion of the molecule, as cationic cobalt tends to react with materials in the reservoir, which leads to inaccurate analytical information. Also, the analytical procedure for detecting the cobalt involves adsorbing the cobalt on an anionic exchange resin, so use of cobalt in the cationic form would not be suitable. Other complex metal anions can be used in the process.

The use of nonradioactive cobaltic hexacyanide as an economic tracer material requires that a very sensitive analytical procedure be available, so that the amount of tracer injected can be low.

An analytical procedure that can detect cobaltic hexacyanide in amounts below 40 parts per trillion has been developed. The basic steps in the procedure are (1) adsorption of cobaltic hexacyanide complex on an anion exchange resin, (2) combustion of the anion exchange resin, (3) acid solubilization of cobalt from the combustion residue, and (4) analysis of the solubilized cobalt by inductively coupled plasma/mass spectrometry, atomic absorption, or other means.

The ability to detect such low amounts of cobaltic hexacyanide means that small amounts of the tracer can be used with good results.

The efficacy of the process has been demonstrated in actual reservoir situations, as exemplified by the following examples:

EXAMPLE I

In a reservoir targeted for carbon dioxide flooding, about 700 g of potassium cobaltic hexacyanide was injected into several injection wells where the wells were on 40-acre spacing in roughly a five spot pattern. The average thickness of the net pay reservoir was 62 feet, the average porosity was 11.7 percent, the injection rate per well was 1,000 barrels per day, and the average production rate per well was 896 barrels per day. The tracer responded in measurable and interpretable concentrations, such that reservoir characteristics could be determined without the need for use of radioactive tracers.

EXAMPLE II

In several West Texas reservoirs tested in a manner similar to that described for Example I, all but one provided measurable and interpretable concentrations of the tracer in produced fluids within four months of tracer injection, and the one that did not show tracer breakthrough in that time period had also failed to provide useful levels of tracer in produced fluid in that time period when conventional tracers were used.

EXAMPLE III

This example describes a procedure for analyzing produced fluid for cobaltic hexacyanide:

Step 1

Cobaltic Hexacyanide Concentration on Anion Exchange Resin

Filter 500 ml of produced water through paper and glass fiber filters.

Pump the 500 -ml filtrate aliquot through a 12"×½" i.d. flexible tube section packed with Bio-Rad AG 1-X8 anion exchange resin (100 mesh, chloride form). An appropriate flow rate through the column is 9 ml per minute. After the sample, rinse the resin column with 100 ml of water containing 5 ml of concentrated HCL.

Transfer the resin from the tube section into a glass vial and dry overnight at approximately 90°C.

Step 2

Resin Combustion

Combust the dry resin by placing the vial in a 550° C. furnace for four hours.

Step 3

Cobalt Solubilization

Cool the combusted resin vial and add 2 ml of concentrated nitric acid and 2 ml of concentrated hydrochloric acid. Cap the vial and vigorously mix for 15 seconds.

Uncap the vial and evaporate its contents to dryness.

After cooling, add 5 ml of water containing 0.1 percent concentrated hydrochloric acid to the vial. Recap the vial and vigorously mix for one minute.

Step 4

Cobalt Analysis

Use inductively coupled plasma/mass spectrometry (ICPMS) to determine the parts per billion cobalt in the 5-ml sample. Convert these results to parts per trillion cobaltic hexacyanide in the original sample using the following equation:

$$A = \frac{B \times C \times D \times E}{F \times G}$$

where,
- A = Cobaltic hexacyanide concentration in original sample in parts per trillion.
- B = Cobalt analytical result in parts per billion.
- C = Volume in liters of acidified water used to dissolve cobalt just prior to ICPMS analysis
- D = Molecular weight of cobaltic hexacyanide.
- E = 1000 parts per trillion/part per billion.
- F = Original produced water sample volume (L).
- G = Atomic weight of cobalt.

We claim:

1. A method for use in determining subterranean reservoir characteristics comprising:
   (a) injecting a tracer material comprising a nonradioactive complex metal anion into said reservoir by means of an injection well;
   (b) injecting a flooding fluid into said injection well following said tracer injection;
   (c) recovering produced fluid from at least one production well which is in fluid communication via said reservoir with said injection well; and
   (d) analyzing said produced fluid for presence of said non-radioactive complex metal anioin tracer to assess said reservoir for enhanced and secondary recovery processes by the following steps;
      (i) passing a sample of said produced fluid through an anion exchange resin;
      (ii) combusting said resin;
      (iii) treating the ash residue from said combustion step to dissolve any metal from said complex metal anion; and
      (iv) analyzing the solution resulting from step (iii) for the presence of said metal.

2. The method of claim 1 wherein said complex metal anion is cobaltic hexacyanide.

3. The method of claim 1 wherein said ash residue is solubilized with acid.

4. The method of claim 3 wherein the acid solution resulting from said solubilization is subjected to atomic absorption analysis.

5. The method of claim 3 wherein the acid solution resulting from said solubilization is subjected to inductively coupled plasma/mass spectrometry.

6. A method for use in determining subterranean reservoir characteristics comprising:
   (a) injecting a tracer material comprising a nonradioactive complex metal anion into an injection well;
   (b) injecting a flooding fluid into said injection well following said tracer injection;
   (c) periodically sampling produced fluid from at least one production well which is in fluid communication via said reservoir with said injection well;
   (d) passing each of said samples through individual anionic exchange resins to adsorb anionic material from said sampled fluid; and
   (e) analyzing said anionic exchange resin to determine the presence of, and amount of, the metal component of said complex metal anion.

* * * * *